(12) United States Patent
Chihara

(10) Patent No.: US 6,238,915 B1
(45) Date of Patent: May 29, 2001

(54) MUTANT HUMAN GROWTH HORMONES AND THEIR USES

(75) Inventor: Kazuo Chihara, Kobe (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 08/800,215

(22) Filed: Feb. 12, 1997

(30) Foreign Application Priority Data

Feb. 13, 1996 (JP) .................................................. 8-050940
Jun. 18, 1996 (JP) .................................................. 8-178643

(51) Int. Cl.⁷ .......................... C12N 15/63; C12N 15/18; C07K 14/61; A61K 38/27
(52) U.S. Cl. ........................ 435/320.1; 435/69.4; 514/12; 530/399; 930/120
(58) Field of Search .......................... 530/399; 435/69.4, 435/252.3, 320.1, 325; 536/23.51; 514/12

(56) References Cited

U.S. PATENT DOCUMENTS 5,350,836 * 9/1994 Kopchick et al. .................... 530/399
5,534,617 * 7/1996 Cunningham et al. .............. 530/399
5,580,723 * 12/1996 Wells et al. ............................... 435/6

FOREIGN PATENT DOCUMENTS 0 319 049   6/1989 (EP) .
92 19736   11/1992 (WO) .

OTHER PUBLICATIONS

*Biochemical and Biophysical Research Communications*, vol. 172, No. 1, Oct. 15, 1990, pp. 357–363.
Sigma Molecular Biology Catalog, p. 73. 1993.*

* cited by examiner

*Primary Examiner*—Christine J. Saoud
(74) *Attorney, Agent, or Firm*—Jacobson, Price, Holman & Stern, PLLC

(57) ABSTRACT

In accordance with the present invention, there are provided mutant human growth hormone proteins which exhibit enhanced affinity for growth hormone but lowered hormone activity, base sequences encoding the same and their production processes as well as uses of said proteins. The proteins according to the present invention, with their enhanced affinities for the growth hormone receptor, can inhibit the binding of growth hormone to its receptor, while they retain lowered growth hormone activities, thus finding application as a medicament for the treatment of acromegaly and gigantism.

8 Claims, 9 Drawing Sheets

FIG. 1

```
     5'         9          18          27          36          45          54
        TTC CCA ACC ATT CCC TTA TCC AGG CCT TTT GAC AAC GCT ATG CTC CGC GCC CAT
        ─── ─── ─── ─── ─── ─── ─── ─── ─── ─── ─── ─── ─── ─── ─── ─── ─── ───
         F   P   T   I   P   L   S   R   P   F   D   N   A   M   L   R   A   H 63          72          81          90          99         108
        CGT CTG CAC CAG CTG GCC TTT GAC ACC TAC CAG GAG TTT GAA GAA GCC TAT ATC
        ─── ─── ─── ─── ─── ─── ─── ─── ─── ─── ─── ─── ─── ─── ─── ─── ─── ───
         R   L   H   Q   L   A   F   D   T   Y   Q   E   F   E   E   A   Y   I 117         126         135         144         153         162
        CCA AAG GAA CAG AAG TAT TCA TTC CTG CAG AAC CCC CAG ACC TCC CTC TGT TTC
        ─── ─── ─── ─── ─── ─── ─── ─── ─── ─── ─── ─── ─── ─── ─── ─── ─── ───
         P   K   E   Q   K   Y   S   F   L   Q   N   P   Q   T   S   L   C   F 171         180         189         198         207         216
        TCA GAG TCT ATT CCG ACA CCC TCC AAC AGG GAG GAA ACA CAA CAG AAA TCC AAC
        ─── ─── ─── ─── ─── ─── ─── ─── ─── ─── ─── ─── ─── ─── ─── ─── ─── ───
         S   E   S   I   P   T   P   S   N   R   E   E   T   Q   Q   K   S   N 225         234         243         252         261         270
        CTA GAG CTG CTC TGC ATC TCC CTG CTG CTC ATC CAG TCG TGG CTG GAG CCC GTG
        ─── ─── ─── ─── ─── ─── ─── ─── ─── ─── ─── ─── ─── ─── ─── ─── ─── ───
         L   E   L   L   C   I   S   L   L   L   I   Q   S   W   L   E   P   V 279         288         297         306         315         324
        CAG TTC CTC AGG AGT GTC TTC GCC AAC AGC CTG GTG TAC GGC GCC TCT GAC AGC
        ─── ─── ─── ─── ─── ─── ─── ─── ─── ─── ─── ─── ─── ─── ─── ─── ─── ───
         Q   F   L   R   S   V   F   A   N   S   L   V   Y   G   A   S   D   S 333         342         351         360         369         378
        AAC GTC TAT GAC CTC CTA AAG GAC CTA GAG GAA GGC ATC CAA ACG CTG ATG GGG
        ─── ─── ─── ─── ─── ─── ─── ─── ─── ─── ─── ─── ─── ─── ─── ─── ─── ───
         N   V   Y   D   L   L   K   D   L   E   E   G   I   Q   T   L   M   G 387         396         405         414         423         432
        AGG CTG GAA GAT GGC AGC CCC CGG ACT GGG CAG ATC TTC AAG CAG ACC TAC AGC
        ─── ─── ─── ─── ─── ─── ─── ─── ─── ─── ─── ─── ─── ─── ─── ─── ─── ───
         R   L   E   D   G   S   P   R   T   G   Q   I   F   K   Q   T   Y   S 441         450         459         468         477         486
        AAG TTC GAC ACA AAC TCA CAC AAC GAT GAC GCA CTA CTC AAG AAC TAC GGG CTG
        ─── ─── ─── ─── ─── ─── ─── ─── ─── ─── ─── ─── ─── ─── ─── ─── ─── ───
         K   F   D   T   N   S   H   N   D   D   A   L   L   K   N   Y   G   L 495         504         513         522         531         540
        CTC TAC TGC TTC AGG AAG GAC ATG GAC AAG GTC GAG ACA TTC CTG CGC ATC GTG
        ─── ─── ─── ─── ─── ─── ─── ─── ─── ─── ─── ─── ─── ─── ─── ─── ─── ───
         L   Y   C   F   R   K   D   M   D   K   V   E   T   F   L   R   I   V 549         558         567
        CAG TGC CGC TCT GTG GAG GGC AGC TGT GGC TTC   3'
        ─── ─── ─── ─── ─── ─── ─── ─── ─── ─── ───
         Q   C   R   S   V   E   G   S   C   G   F
```

FIG. 2

```
5'        9         18        27        36        45        54
   TTC CCA ACC ATT CCC TTA TCC AGG CCT TTT GAC AAC GCT ATG CTC CGC GCC CAT
    F   P   T   I   P   L   S   R   P   F   D   N   A   M   L   R   A   H 63        72        81        90        99        108
   CGT CTG CAC CAG CTG GCC TTT GAC ACC TAC CAG GAG TTT GAA GAA GCC TAT ATC
    R   L   H   Q   L   A   F   D   T   Y   Q   E   F   E   E   A   Y   I 117       126       135       144       153       162
   CCA AAG GAA CAG AAG TAT TCA TTC CTG CAG AAC CCC CAG ACC TCC CTC GCT TTC
    P   K   E   Q   K   Y   S   F   L   Q   N   P   Q   T   S   L   A   F 171       180       189       198       207       216
   TCA GAG TCT ATT CCG ACA CCC TCC AAC AGG GAG GAA ACA CAA CAG AAA TCC AAC
    S   E   S   I   P   T   P   S   N   R   E   E   T   Q   Q   K   S   N 225       234       243       252       261       270
   CTA GAG CTG CTC TGC ATC TCC CTG CTG CTC ATC CAG TCG TGG CTG GAG CCC GTG
    L   E   L   L   C   I   S   L   L   L   I   Q   S   W   L   E   P   V 279       288       297       306       315       324
   CAG TTC CTC AGG AGT GTC TTC GCC AAC AGC CTG GTG TAC GGC GCC TCT GAC AGC
    Q   F   L   R   S   V   F   A   N   S   L   V   Y   G   A   S   D   S 333       342       351       360       369       378
   AAC GTC TAT GAC CTC CTA AAG GAC CTA GAG GAA GGC ATC CAA ACG CTG ATG GGG
    N   V   Y   D   L   L   K   D   L   E   E   G   I   Q   T   L   M   G 387       396       405       414       423       432
   AGG CTG GAA GAT GGC AGC CCC CGG ACT GGG CAG ATC TTC AAG CAG ACC TAC AGC
    R   L   E   D   G   S   P   R   T   G   Q   I   F   K   Q   T   Y   S 441       450       459       468       477       486
   AAG TTC GAC ACA AAC TCA CAC AAC GAT GAC GCA CTA CTC AAG AAC TAC GGG CTG
    K   F   D   T   N   S   H   N   D   D   A   L   L   K   N   Y   G   L 495       504       513       522       531       540
   CTC TAC TGC TTC AGG AAG GAC ATG GAC AAG GTC GAG ACA TTC CTG CGC ATC GTG
    L   Y   C   F   R   K   D   M   D   K   V   E   T   F   L   R   I   V 549       558       567
   CAG TGC CGC TCT GTG GAG GGC AGC TGT GGC TTC    3'
    Q   C   R   S   V   E   G   S   C   G   F
```

FIG. 3

```
5'      9           18          27          36          45          54
    TTC CCA ACC ATT CCC TTA TCC AGG CCT TTT GAC AAC GCT ATG CTC CGC GCC CAT
     F   P   T   I   P   L   S   R   P   F   D   N   A   M   L   R   A   H 63          72          81          90          99          108
    CGT CTG CAC CAG CTG GCC TTT GAC ACC TAC CAG GAG TTT GAA GAA GCC TAT ATC
     R   L   H   Q   L   A   F   D   T   Y   Q   E   F   E   E   A   Y   I 117         126         135         144         153        162
    CCA AAG GAA CAG AAG TAT TCA TTC CTG CAG AAC CCC CAG ACC TCC CTC TGT TTC
     P   K   E   Q   K   Y   S   F   L   Q   N   P   Q   T   S   L   C   F 171         180         189         198         207         216
    TCA GAG TCT ATT CCG ACA CCC TCC AAC AGG GAG GAA ACA CAA CAG AAA TCC AAC
     S   E   S   I   P   T   P   S   N   R   E   E   T   Q   Q   K   S   N 225        234         243         252         261         270
    CTA GAG CTG CTC TGC ATC TCC CTG CTG CTC ATC CAG TCG TGG CTG GAG CCC GTG
     L   E   L   L   C   I   S   L   L   L   I   Q   S   W   L   E   P   V 279         288         297         306         315         324
    CAG TTC CTC AGG AGT GTC TTC GCC AAC AGC CTG GTG TAC GGC GCC TCT GAC AGC
     Q   F   L   R   S   V   F   A   N   S   L   V   Y   G   A   S   D   S 333         342         351         360         369         378
    AAC GTC TAT GAC CTC CTA AAG GAC CTA GAG GAA GGC ATC CAA ACG CTG ATG GGG
     N   V   Y   D   L   L   K   D   L   E   E   G   I   Q   T   L   M   G 387         396         405         414         423         432
    AGG CTG GAA GAT GGC AGC CCC CGG ACT GGG CAG ATC TTC AAG CAG ACC TAC AGC
     R   L   E   D   G   S   P   R   T   G   Q   I   F   K   Q   T   Y   S 441         450         459         468         477         486
    AAG TTC GAC ACA AAC TCA CAC AAC GAT GAC GCA CTA CTC AAG AAC TAC GGG CTG
     K   F   D   T   N   S   H   N   D   D   A   L   L   K   N   Y   G   L 495         504         513         522         531         540
            CTC TAC GCC TTC AGG AAG GAC ATG GAC AAG GTC GAG ACA TTC CTG CGC ATC GTG
             L   Y   A   F   R   K   D   M   D   K   V   E   T   F   L   R   I   V 549         558         567
    CAG TGC CGC TCT GTG GAG GGC AGC TGT GGC TTC  3'
     Q   C   R   S   V   E   G   S   C   G   F
```

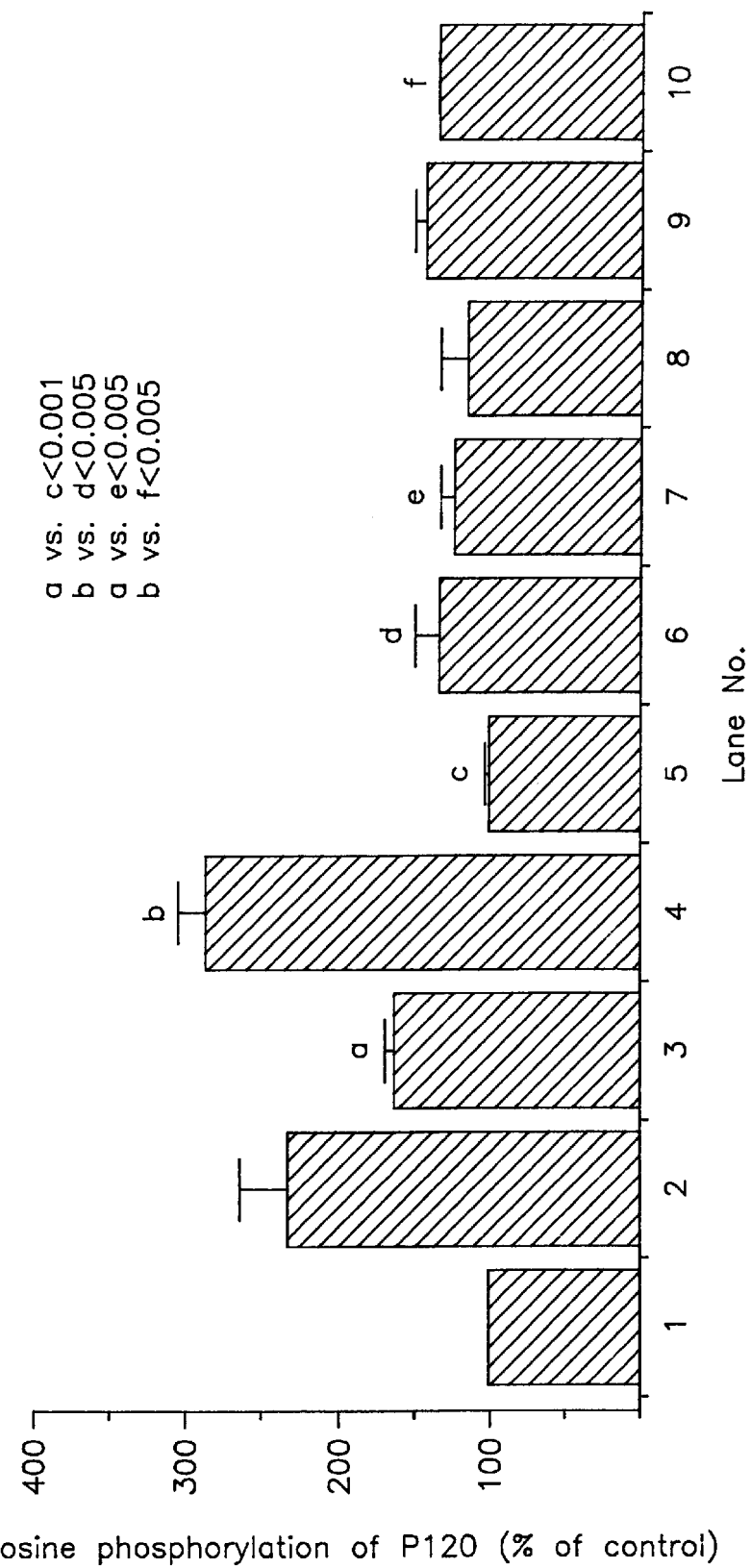

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:1:

ACAGAAACAG GTGGGGGCAA                                                    20

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AATAGACTCT GAGAAAGCGG G                                                  21

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GTCCATGTCC TTCCTGAAGG CGTAGAG                                            27

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TATGAATTCC TCTGCCTGCC CTGCCTCAAG AG                                      32

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CTAACACAGT CTCTCAAAGT                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ACTTTGAGAG ACTGTGTTAG                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TGGAGTGGCA ACTTCCAGGG                                              20

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CTCAGGGTCC TGTGGACAGC TCACCTAGCT GCA                               33

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TGGACAGCTC ACCTAGCTGC A                                            21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGATTTCTGT TGTGTTTCCT                                              20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TTGACACCTA CCAGGAGTTT                                              20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
CTAGAAGCCA CAGCTGCCCT                                             20
```

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
TAAGAATTCG AGGGGTCACA GGGATGCCAC CCC                              33
```

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
GCGGATCCTT CCCAACCATT CCCTTATC                                    28
```

(2) INFORMATION FOR SEQ ID NO:15:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO:15:

```
TTC CCA ACC ATT CCC TTA TCC AGG CCT TTT GAC AAC GCT ATG CTC CGC    48
Phe Pro Thr Ile Pro Leu Ser Arg Pro Phe Asp Asn Ala Met Leu Arg
 1               5                  10                  15

GCC CAT CGT CTG CAC CAG CTG GCC TTT GAC ACC TAC CAG GAG TTT GAA    96
Ala His Arg Leu His Gln Leu Ala Phe Asp Thr Tyr Gln Glu Phe Glu
             20                  25                  30

GAA GCC TAT ATC CCA AAG GAA CAG AAG TAT TCA TTC CTG CAG AAC CCC   144
Glu Ala Tyr Ile Pro Lys Glu Gln Lys Tyr Ser Phe Leu Gln Asn Pro
         35                  40                  45

CAG ACC TCC CTC TGT TTC TCA GAG TCT ATT CCG ACA CCC TCC AAC AGG   192
Gln Thr Ser Leu Cys Phe Ser Glu Ser Ile Pro Thr Pro Ser Asn Arg
     50                  55                  60

GAG GAA ACA CAA CAG AAA TCC AAC CTA GAG CTG CTC TGC ATC TCC CTG   240
```

```
Glu Glu Thr Gln Gln Lys Ser Asn Leu Glu Leu Leu Cys Ile Ser Leu
 65                  70                  75                  80

CTG CTC ATC CAG TCG TGG CTG GAG CCC GTG CAG TTC CTC AGG AGT GTC        288
Leu Leu Ile Gln Ser Trp Leu Glu Pro Val Gln Phe Leu Arg Ser Val
                 85                  90                  95

TTC GCC AAC AGC CTG GTG TAC GGC GCC TCT GAC AGC AAC GTC TAT GAC        336
Phe Ala Asn Ser Leu Val Tyr Gly Ala Ser Asp Ser Asn Val Tyr Asp
             100                 105                 110

CTC CTA AAG GAC CTA GAG GAA GGC ATC CAA ACG CTG ATG GGG AGG CTG        384
Leu Leu Lys Asp Leu Glu Glu Gly Ile Gln Thr Leu Met Gly Arg Leu
         115                 120                 125

GAA GAT GGC AGC CCC CGG ACT GGG CAG ATC TTC AAG CAG ACC TAC AGC        432
Glu Asp Gly Ser Pro Arg Thr Gly Gln Ile Phe Lys Gln Thr Tyr Ser
     130                 135                 140

AAG TTC GAC ACA AAC TCA CAC AAC GAT GAC GCA CTA CTC AAG AAC TAC        480
Lys Phe Asp Thr Asn Ser His Asn Asp Asp Ala Leu Leu Lys Asn Tyr
145                 150                 155                 160

GGG CTG CTC TAC TGC TTC AGG AAG GAC ATG GAC AAG GTC GAG ACA TTC        528
Gly Leu Leu Tyr Cys Phe Arg Lys Asp Met Asp Lys Val Glu Thr Phe
                 165                 170                 175

CTG CGC ATC GTG CAG TGC CGC TCT GTG GAG GGC AGC TGT GGC TTC            573
Leu Arg Ile Val Gln Cys Arg Ser Val Glu Gly Ser Cys Gly Phe
             180                 185                 190

(2) INFORMATION FOR SEQ ID NO:16:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:16:

Phe Pro Thr Ile Pro Leu Ser Arg Pro Phe Asp Asn Ala Met Leu Arg
  1               5                  10                  15

Ala His Arg Leu His Gln Leu Ala Phe Asp Thr Tyr Gln Glu Phe Glu
                 20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
         50                  55                  60

Glu Glu Thr Gln Gln Lys Ser Asn Leu Glu Leu Leu Cys Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
             100                 105                 110

Leu Leu Lys Asp Leu Glu Glu Gly Ile Gln Thr Leu Met Gly Arg Leu
         115                 120                 125

Glu Asp Gly Ser Pro Arg Thr Gly Gln Ile Phe Lys Gln Thr Tyr Ser
     130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                 165                 170                 175

Leu Arg Ile Val Gln Cys Arg Ser Val Glu Gly Ser Cys Gly Phe
             180                 185                 190
```

(2) INFORMATION FOR SEQ ID NO:17:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO:17:

```
TTC CCA ACC ATT CCC TTA TCC AGG CCT TTT GAC AAC GCT ATG CTC CGC      48
Phe Pro Thr Ile Pro Leu Ser Arg Pro Phe Asp Asn Ala Met Leu Arg
 1               5                  10                  15

GCC CAT CGT CTG CAC CAG CTG GCC TTT GAC ACC TAC CAG GAG TTT GAA      96
Ala His Arg Leu His Gln Leu Ala Phe Asp Thr Tyr Gln Glu Phe Glu
             20                  25                  30

GAA GCC TAT ATC CCA AAG GAA CAG AAG TAT TCA TTC CTG CAG AAC CCC     144
Glu Ala Tyr Ile Pro Lys Glu Gln Lys Tyr Ser Phe Leu Gln Asn Pro
         35                  40                  45

CAG ACC TCC CTC GCT TTC TCA GAG TCT ATT CCG ACA CCC TCC AAC AGG     192
Gln Thr Ser Leu Ala Phe Ser Glu Ser Ile Pro Thr Pro Ser Asn Arg
 50                  55                  60

GAG GAA ACA CAA CAG AAA TCC AAC CTA GAG CTG CTC TGC ATC TCC CTG     240
Glu Glu Thr Gln Gln Lys Ser Asn Leu Glu Leu Leu Cys Ile Ser Leu
 65                  70                  75                  80

CTG CTC ATC CAG TCG TGG CTG GAG CCC GTG CAG TTC CTC AGG AGT GTC     288
Leu Leu Ile Gln Ser Trp Leu Glu Pro Val Gln Phe Leu Arg Ser Val
                 85                  90                  95

TTC GCC AAC AGC CTG GTG TAC GGC GCC TCT GAC AGC AAC GTC TAT GAC     336
Phe Ala Asn Ser Leu Val Tyr Gly Ala Ser Asp Ser Asn Val Tyr Asp
            100                 105                 110

CTC CTA AAG GAC CTA GAG GAA GGC ATC CAA ACG CTG ATG GGG AGG CTG     384
Leu Leu Lys Asp Leu Glu Glu Gly Ile Gln Thr Leu Met Gly Arg Leu
        115                 120                 125

GAA GAT GGC AGC CCC CGG ACT GGG CAG ATC TTC AAG CAG ACC TAC AGC     432
Glu Asp Gly Ser Pro Arg Thr Gly Gln Ile Phe Lys Gln Thr Tyr Ser
130                 135                 140

AAG TTC GAC ACA AAC TCA CAC AAC GAT GAC GCA CTA CTC AAG AAC TAC     480
Lys Phe Asp Thr Asn Ser His Asn Asp Asp Ala Leu Leu Lys Asn Tyr
145                 150                 155                 160

GGG CTG CTC TAC TGC TTC AGG AAG GAC ATG GAC AAG GTC GAG ACA TTC     528
Gly Leu Leu Tyr Cys Phe Arg Lys Asp Met Asp Lys Val Glu Thr Phe
                165                 170                 175

CTG CGC ATC GTG CAG TGC CGC TCT GTG GAG GGC AGC TGT GGC TTC         573
Leu Arg Ile Val Gln Cys Arg Ser Val Glu Gly Ser Cys Gly Phe
            180                 185                 190
```

(2) INFORMATION FOR SEQ ID NO:18:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:18:

```
Phe Pro Thr Ile Pro Leu Ser Arg Pro Phe Asp Asn Ala Met Leu Arg
 1               5                  10                  15
```

```
Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Ala Phe Ser Glu Ser Ile Pro Thr Pro Ser Asn Arg
    50                  55                  60

Glu Glu Thr Gln Gln Lys Ser Asn Leu Glu Leu Leu Cys Ile Ser Leu
65                  70                  75                  80

Leu Leu Ile Gln Ser Trp Leu Glu Pro Val Gln Phe Leu Arg Ser Val
            85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
            165                 170                 175

Leu Arg Ile Val Gln Cys Arg Ser Val Glu Gly Ser Cys Gly Phe
            180                 185                 190

(2) INFORMATION FOR SEQ ID NO:19:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO:19:

TTC CCA ACC ATT CCC TTA TCC AGG CCT TTT GAC AAC GCT ATG CTC CGC        48
Phe Pro Thr Ile Pro Leu Ser Arg Pro Phe Asp Asn Ala Met Leu Arg
 1               5                  10                  15

GCC CAT CGT CTG CAC CAG CTG GCC TTT GAC ACC TAC CAG GAG TTT GAA        96
Ala His Arg Leu His Gln Leu Ala Phe Asp Thr Tyr Gln Glu Phe Glu
            20                  25                  30

GAA GCC TAT ATC CCA AAG GAA CAG AAG TAT TCA TTC CTG CAG AAC CCC       144
Glu Ala Tyr Ile Pro Lys Glu Gln Lys Tyr Ser Phe Leu Gln Asn Pro
        35                  40                  45

CAG ACC TCC CTC TGT TTC TCA GAG TCT ATT CCG ACA CCC TCC AAC AGG       192
Gln Thr Ser Leu Cys Phe Ser Glu Ser Ile Pro Thr Pro Ser Asn Arg
    50                  55                  60

GAG GAA ACA CAA CAG AAA TCC AAC CTA GAG CTG CTC TGC ATC TCC CTG       240
Glu Glu Thr Gln Gln Lys Ser Asn Leu Glu Leu Leu Cys Ile Ser Leu
65                  70                  75                  80

CTG CTC ATC CAG TCG TGG CTG GAG CCC GTG CAG TTC CTC AGG AGT GTC       288
Leu Leu Ile Gln Ser Trp Leu Glu Pro Val Gln Phe Leu Arg Ser Val
            85                  90                  95

TTC GCC AAC AGC CTG GTG TAC GGC GCC TCT GAC AGC AAC GTC TAT GAC       336
Phe Ala Asn Ser Leu Val Tyr Gly Ala Ser Asp Ser Asn Val Tyr Asp
            100                 105                 110
```

```
CTC CTA AAG GAC CTA GAG GAA GGC ATC CAA ACG CTG ATG GGG AGG CTG     384
Leu Leu Lys Asp Leu Glu Glu Gly Ile Gln Thr Leu Met Gly Arg Leu
        115                 120                 125

GAA GAT GGC AGC CCC CGG ACT GGG CAG ATC TTC AAG CAG ACC TAC AGC     432
Glu Asp Gly Ser Pro Arg Thr Gly Gln Ile Phe Lys Gln Thr Tyr Ser
    130                 135                 140

AAG TTC GAC ACA AAC TCA CAC AAC GAT GAC GCA CTA CTC AAG AAC TAC     480
Lys Phe Asp Thr Asn Ser His Asn Asp Asp Ala Leu Leu Lys Asn Tyr
145                 150                 155                 160

GGG CTG CTC TAC GCC TTC AGG AAG GAC ATG GAC AAG GTC GAG ACA TTC     528
Gly Leu Leu Tyr Ala Phe Arg Lys Asp Met Asp Lys Val Glu Thr Phe
                165                 170                 175

CTG CGC ATC GTG CAG TGC CGC TCT GTG GAG GGC AGC TGT GGC TTC         573
Leu Arg Ile Val Gln Cys Arg Ser Val Glu Gly Ser Cys Gly Phe
            180                 185                 190
```

(2) INFORMATION FOR SEQ ID NO:20:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:20:

```
Phe Pro Thr Ile Pro Leu Ser Arg Pro Phe Asp Asn Ala Met Leu Arg
 1               5                  10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Cys Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Ala Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

(2) INFORMATION FOR SEQ ID NO:21:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA

```
       (xi) SEQUENCE DESCRIPTION: SEQ ID NO:21:

CTGCTCYGCA TC                                                                   12

(2) INFORMATION FOR SEQ ID NO:22:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:22:

CTGCTCCGCA TC                                                                   12
```

MUTANT HUMAN GROWTH HORMONES AND THEIR USES

The present invention relates to a mutant human growth hormone protein having an amino acid sequence given in FIG. 1, to a deoxyribonucleotides showing a base sequence which encodes said amino acid sequence, to mutant human growth hormone proteins each having an amino acid sequence subjected to partial replacement, insertion or deletion to such an extent as may not cause loss of its characteristic features such as enhanced affinity for the growth hormone receptor is exhibited and decreased growth hormone activity, and to their uses in the manufacture of medicaments for the treatment of gigantism and acromegaly.

BACKGROUND OF THE INVENTION

The biologically inactive human growth hormones according to the present invention act as an antagonist of normal growth hormone for its receptor to thereby inhibit the disturbances and excessive growth caused by oversecretion, and can be utilized as a medicament with improved safety for the treatment of gigantism and acromegaly.

As the genetic disorders brought about by growth hormone, there are known growth retardation due to a deficiency of growth hormone as well as gigantism and acromegaly owing to excessive expression. For the growth hormone deficiency, supplementation therapy with growth hormone has been in wide use, but no effective drug has been developed so far for the treatment of gigantism and acromegaly.

In 1978, Kowarski et al. reported for the first time the discovery of a biologically inactive growth hormone (a mutant growth hormone) (Kowarski, A. A. et al., J. Clin. Endocrinol. Metab., 47: 461, 1978). However, understanding of the mutant growth hormone at the molecular level has not yet been elucidated up to now, although there was published a report that an abnormal polymer of growth hormone was identified in the blood from a child with dwarfism (Valena, L. J. et al., N. Engl. J. Med., 312:214, 1985). A child, who was found to contain a biologically inactive growth hormone in the circulatory blood, showed a high blood level of a mutant growth hormone but a low blood concentration of insulin-like growth factor (IGF-1), thereby causing retarded growth and development. However, such growth retardation is characterized by good response to normal growth hormone administered (Hayek A. et al., Pediatr. Res., 12: 413, 1973; Rudman, D. et al., N. Engl. J. Med., 305: 123, 1981; Plotnick, L. P. et al., Pediatrics 71: 324, 1983; Bright, G. M. et al., 71:576, 1983).

In recent years, progresses in protein engineering and genetic engineering have enabled structural research to be conducted on the binding of hormones to their receptors as well as the elicitation of their activities, and as a result, the causes for various genetic diseases have been clarified.

Cunningham et al. prepared a number of human growth hormone variants by using protein engineering procedures to conduct investigation on their binding sites for the growth hormone receptor, and as a result, identified the region being involved in the binding of growth hormone to the receptor, which constitutes a region consisting of the amino-terminal (2–19) amino acid residue, the carboxy-terminal (54–74) amino acid terminal and the carboxy-terminal (167–191) amino acid residue (Cunningham, B. C. et al., Science 243: 1330, 1989).

Furthermore, Uchida et al. prepared growth hormone variants having amino acid residues subjected to different replacements to thereby measure their differentiating activities for 3T3-F 442A cells, leading to the suggestion that the amino acid sequence 62 to 67 region is of critical importance to the development of biological activity (Uchida et al., Biochem. Biophys. Res. Commun., 172: 352, 1990).

Recently, a crystallographic study yielded a remarkable finding on the mode of binding of human growth hormone to its binding protein (a portion of the receptor protein) (De Vos A. M. et al., Science 255: 306, 1992); it is assumed that growth hormone binds consecutively to the growth hormone receptor in a manner where the domain 1 of growth hormone in the first place binds to the first growth hormone receptor and then the second domain 2 of growth hormone binds to the second growth hormone receptor, resulting in the formation of a dimer of the growth hormone receptor, whereupon signals of growth hormone are transmitted into cells.

Interesting among others is the fact that although the domain 1 of human growth hormone differs in amino acid residue from the domain 2, the binding sites of the receptor protein show the common amino acid residue. It was also recognized that growth hormone variants produced by protein engineering techniques binds competitively to the receptor (Fuh G. et al, Science, 256: 1677, 1992).

Recent progresses in gene analysis have made it feasible to identify the abnormal genes being contributed to a large number of genetic diseases. This is the case with the gene for growth hormone which brings about dwarfism, as well. Since growth hormone develops its physiological activity as mediated by the receptor on the cellular membrane, genetic abnormalities associated with growth hormone can roughly be divided into two groups, abnormality in receptor gene and the one in growth hormone itself.

Because growth hormone gene exists on the autosome, furthermore, its abnormalities are known to assume the form of recessive inheritance. In order to allow phenotypic expression of such abnormalities, consequently, it is required that abnormalities are brought about simultaneously in the alleles of the parent.

In the past, there have been reported many cases of growth retardation resulting from the complicated combination of mutations in the parent's growth hormone genes, such as whole depletion, partial depletion and base replacement. When either of the parent is normal, the mutant growth hormone is known to stay inside the intracellular secretory granules.

However, detailed investigation has not yet been conducted on the analysis at the molecular level of mutant growth hormones generated by missense mutation in the living body, as well as its role to be played in the living body. Neither known has been any effective method to suppress the overaction of growth hormone.

SUMMARY OF THE INVENTION

The present inventor found that a 5-years old boy with dwarfism having a delayed bone age showed a high serum concentration of growth hormone and, in the induction test, retained a lowered level of IGF-1, though he exhibited an increased serum concentration of growth hormone, and this finding, followed by further subsequent research, culminated into the present invention.

It seemed likely that this endocrinological finding is consistent with the phenomena noted in the growth hormone insensitivity syndrome (Rosenbloom, A. L., Acta Pediatr. Scand. (Suppl), 383: 117, 1992).

However, consecutive administration of growth hormone brought about a significant improvement in growth of the patient, which excluded the possibility of diagnosing it as the Laron type syndrome, because Laron-type dwarfism is caused by the disorders of growth hormone receptors.

The present inventor, using the Nb2 bioassay method, discovered that the serum growth hormone found in the children suffering from this sort of disorders is an inactive type growth hormone, unlike the one secreted by normal children, and also identified the hormone as a mutant growth hormone by use of isoelectric focusing.

The mutant growth hormone was found to undergo replacement of the arginine residue with the cysteine residue (R→C) at codon 77 of growth hormone (FIG. 1). The site of replacement is located in the second α-helix of growth hormone, behind a site 1 of binding to the receptor (Cunningham, B. C. et al., Science, 254:821, 1991). The substituted cysteine is assumed to form a new disulfide bond and cause the resultant molecule to change the charge, and this brings about conformational alterations, resulting in generation of a mutant growth hormone with reduced growth-hormone activity.

In the intracellular signal transduction of growth hormone, dimerization of the growth hormone receptors through ligand bonding and phosphorylation of the tyrosine residue in their proteins are considered crucially important (Argetsinger, L. S. et al., Cell, 74: 237, 1993: Silva, C. M. et al.: J. Biol. Chem., 269: 27532, 1994).

The growth-hormone binding protein is located in the extracellular domain and functions as a growth hormone reservoir in serum in vivo (Herington, A. C. et al., Acta Endocrinol. (Copenh), 124: 14, 1991).

The affinity of the mutant growth hormone for the growth-hormone binding receptor was found to be about 6 times greater than that of the wild-type one (FIGS. 7 and 8), suggesting that the domains 1 and 2 in the mutant growth hormone show different affinities for the receptor from those in the wild-type one. The biological characteristic of the mutant growth hormone lies in markedly lowered activity of cellular signal transduction developed through phosphorylation of the receptor, despite its greater affinity for the receptor protein.

Wild-type growth hormone, after administered to the patient consecutively for 3 days, did not give rise to conspicuous response to IGF-1, whereas it, when given to the patient over a prolonged period of time, acting as an antagonist to suppress the secretion of endogenous mutant growth hormone as well as its binding to the receptor, was found to be effective in increasing the plasma concentration of IGF-1 and in improving the growth and development.

Consequently, these findings led the present inventor to the conclusion that the mutant growth hormone, when administered to patients with gigantism or acromegaly caused by oversecreted growth hormone, may act as an antagonist to suppress their excessive growth.

The present invention has been completed on the basis of the above novel findings and relates to (1) a mutant human growth hormone protein showing an amino acid sequence given in FIG. 1, (2) a deoxyribonucleotides showing a base sequence which encodes said amino acid sequence, (3) mutant human growth hormone proteins each showing an amino acid sequence which has its amino acid residue moiety subjected to partial replacement, insertion or depletion to such an extent as may not cause loss of its characteristic features that enhanced affinity for the growth hormone receptor is exhibited and that decreased growth hormone activity is retained, and (4) uses thereof.

DETAILED DESCRIPTION OF THE PREFERRED EMBODIMENT

The mutant human growth hormones of the present invention, because of their endogenous identity, do not exert any adverse effects to the living body, while they only induce growth retardation, and can therefore find application as an effective medicament for the treatment of gigantism and acromegaly, against which diseases no therapeutic agent has been developed in the past. The mutant growth hormones exhibit about 6 times greater receptor affinity and are useful as a medicament for the treatment of gigantism at doses equal to or smaller than the dose employed in the treatment of dwarfism.

In accordance with the known art, it is easily and practically feasible to subject the DNA of the novel mutant growth hormone of the present invention to partial depletion, insertion or substitution of nucleotides to thereby produce growth hormone variants showing enhanced receptor affinity but substantially being free from hormone activity, as being exemplified by the sequences illustrated in FIGS. 2 and 3. By using the protein engineering techniques, furthermore, it is possible not only to identify the site of binding of the mutant growth hormone to the receptor but also to produce the peptide of such binding site to thereby utilize the same as a medicament for the treatment of gigantism and acromegaly.

The novel mutant growth hormone of the present invention can be produced by linking the hormone encoding DNA to a reproducible plasmid, then transforming cells with the plasmid and cultivating these host cells. Such host cells include bacteria, yeasts and animal cells.

Prokaryotic cells, such as bacteria, are suited for cloning of desoxyribonucleotides. For example, plasmid pBR 322 derived from *E. coli* contains a gene being resistant to ampicillin or tetracycline, and provides a practical means for identifying the resultant transformed cells. Furthermore, bacterial plasmids contain promoters which can function and operate in the expression of their own proteins.

In addition to prokaryotic cells, eukaryotic cells inclusive of yeasts are of use, as well, and plasmid YRp7 is employable commonly in the expression in Saccharomyces, a strain of yeasts (Stinchcomb et al., Nature, 282: 39, 1979).

Animal cells are also utilized as a host cell, and their cell lines include, for example, Hela cells, CHO (Chinese hamster ovary) cells, COSM6 and COS-7, whereby the promoters of polyoma viruses, adenovirus 2, cytomegalo-viruses and simian viruses serve a useful purpose to act to control the expression plasmids of such cell lines (Thomsen et al., PNAS, 81: 659, 1984).

Animals can be immunized with the mutant growth hormone or its variants to thereby produce their antibodies. Additionally, animals can be immunized by the known techniques to prepare monoclonal antibodies from cells capable of secreting specific antibodies.

In accordance with the present invention, it is facilitated to prepare the mutant growth hormone and its variants in large quantities, and there can be provided their better understanding at the molecular level, which renders it feasible to develop therapeutic and diagnostic agents for the diseases associated with growth hormone. This includes the preparation of drugs for gene therapy, which offer the essential treatment method for such diseases.

The nucleotides for the mutant growth hormones or the nucleotide for the binding-site protein can be incorporated into suitable vectors inclusive of virus vectors from retroviruses, adenoviruses, etc. and this affords a possibility of using them as a drug for gene therapy for gigantism and acromegaly.

BRIEF DESCRIPTION OF THE DRAWINGS

Below described is an example to illustrate the present invention in more detail, with reference to the attached drawings, in which:

FIG. 1 is an amino acid sequence (SEQ ID NO:15) of the mutant growth hormone (the 77-position codon, R→C) obtained in Example 1 and a base sequence encoding its protein (SEQ ID NO:18).

FIG. 2 is an amino acid sequence (SEQ ID NO:16) of the mutant growth hormone having undergone mutation through substitution (the 53 position codon, C→A) obtained in Example 1 and a base sequence encoding its protein (SEQ ID NO:19).

FIG. 3 is an amino acid sequence (SEQ ID NO:17) of the mutant growth hormone (the 165 position codon, C→A) having undergone mutation through substitution obtaine in Example 1 and a base sequence encoding its protein (SEQ ID NO:20).

f1: 5'ACAGAAACAGGTGGGGGCAA3' (SEQ ID NO:1)

R2: 5'AATAGACTCTGAGAAAGCGGG3' (SEQ ID NO:2)

R3: 5'GTCCATGTCCTTCCTGAAGGCGTAGAG3' (SEQ ID NO:3)

PCR amplification was performed using the primers, f1 and R2, for the mutation at the position 53 (C→A), while using the primers, f1 and R3, for the mutation at the position 165 (C→A). Separately, there were prepared the portions downstream of cDNA of normal growth hormone after having been digested with the restriction enzymes HinfI and NIaIII, respectively, followed by binding to the PCR products with a ligase.

Figure 6A:
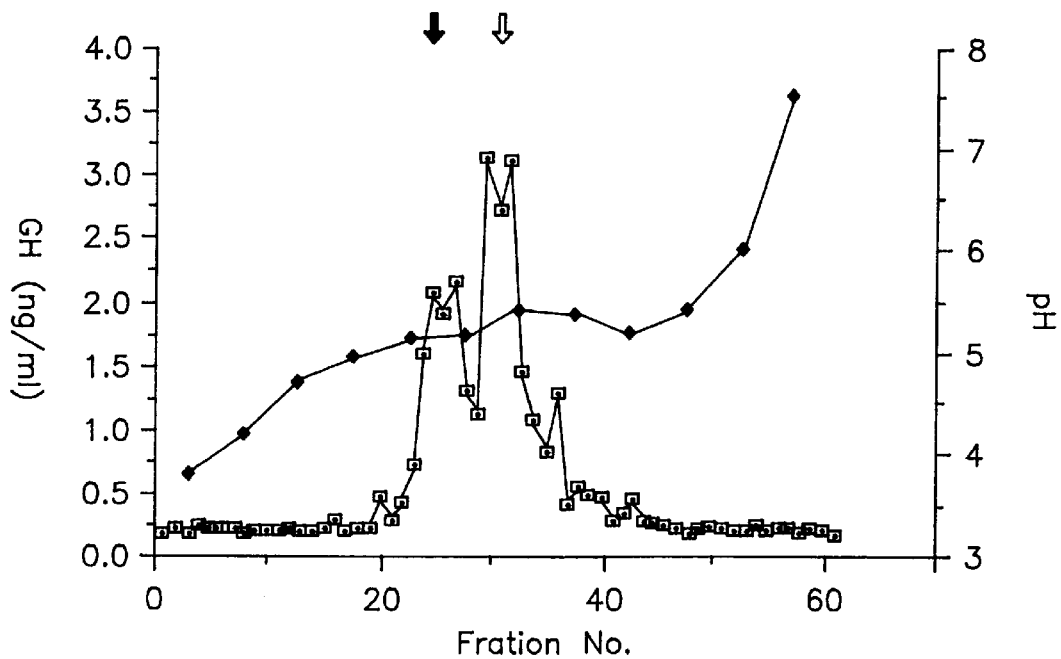
Figure 6B:
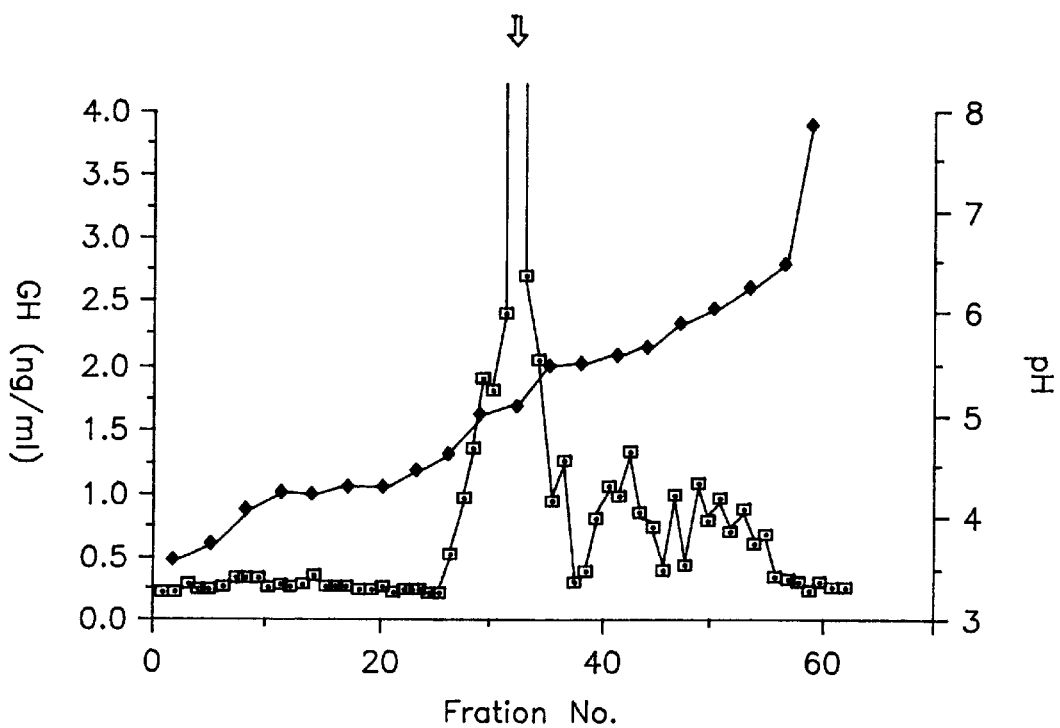
Figure 7A:
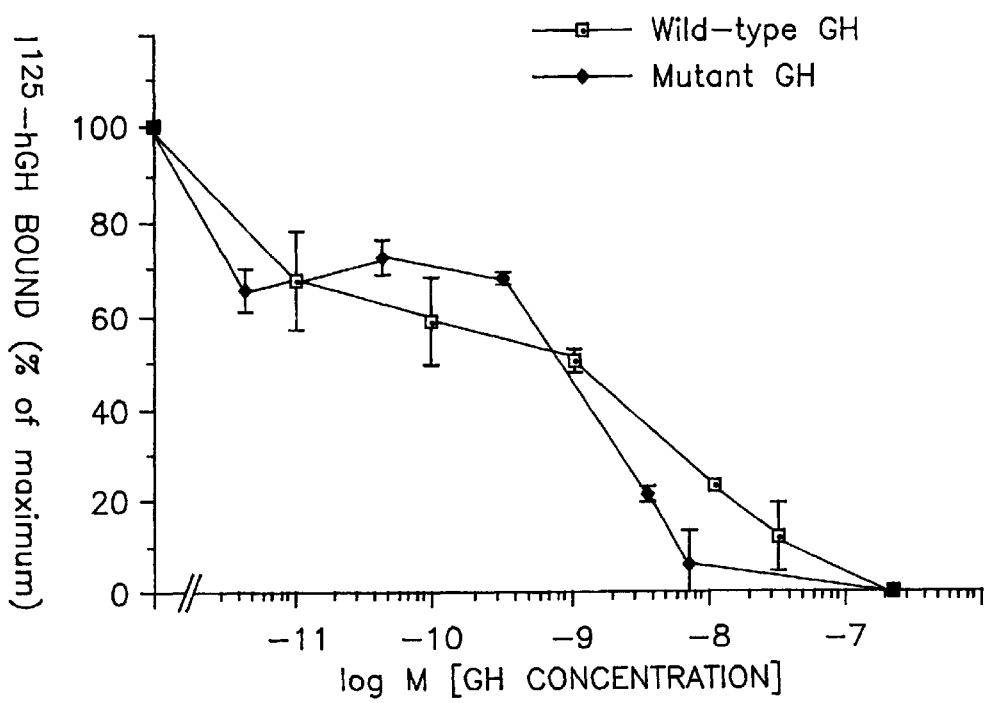

FIGS. 6(A and B) is a graph showing the results of isoelectric focusing (IFE) of the mutant and wild growth hormones in serum. Serum samples (150 to 300 ul) was subjected to isoelectric focusing in 1% HPMC-4% Ampholine (pH 3.5–8.0), and the sample fractions were separated, pooled and assayed for immuoactivity for growth hormone (□), with the pH gradient formed during IEF being designated by (♦). The mutation through substitution of cysteine for arginine is assumed to bring about an isoelectrical decrease by pH 0.16. The peaks for wild type and mutant growth hormones are designated by the white and black arrows, respectively. a; Proband (patient: a boy) b: father FIG. 7a is a graph showing how wild type and mutant growth hormones inhibited binding of [$^{125}$I]-labeled human growth hormone to IM-9 cells.

Cells (IM-9) at the final concentration of 1–3×10$^7$/ml were incubated, while adding wild-type and mutant growth hormones at increased concentrations in accordance with their addition-concentration dependencies: 0.8 ng/ml of [$^{125}$I]-labeled human growth hormone (Du'Pont, USA) (0.33 uCi/ml), 250 ul of the total solution, 30° C. After cultivation for 4 hours, the cells were collected, washed and assayed for radioactivity bound to the cells.

Figure 7B:
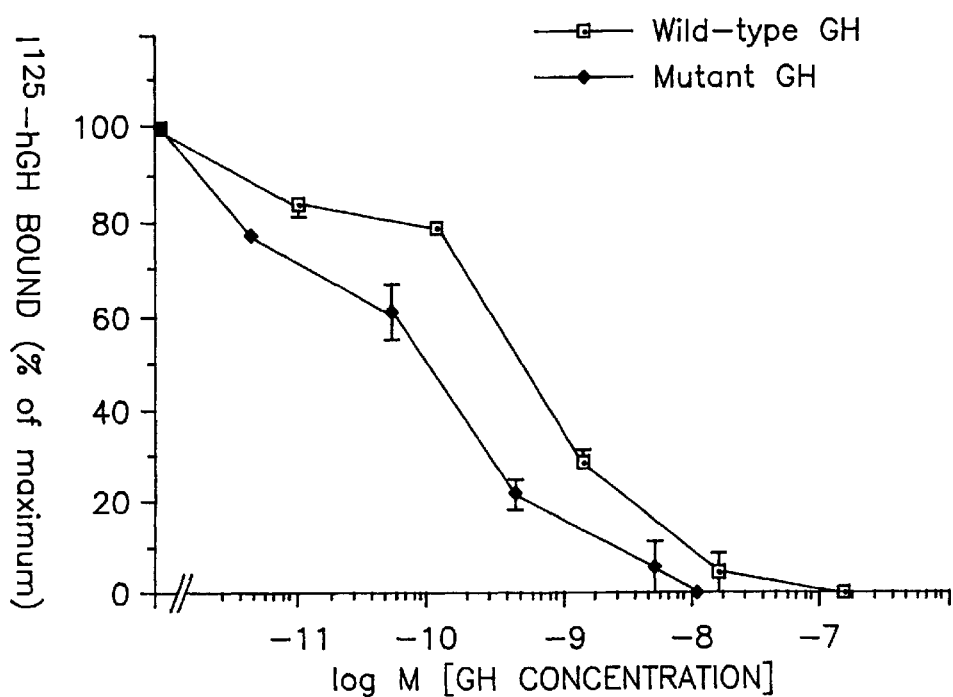

FIG. 7b is a graph showing inhibition of binding of [$^{125}$I]-labeled human growth hormone to the growth-hormone bidning protein.

[$^{125}$I]-Labeled human growth hormone (0.6 uCi/ml), recombinant human growth hormone binding protein (0.6 nM) and anti-growth hormone receptor mouse clonal antibody (Mab 263; AGEN, Australia) (1:100,000) were cultivated at 4° C. for 16 hours, while increasing the respective concentrations of wild-type and mutant growth hormones, followed by addition of 10% anti-mouse IgG (goat) antibody (50 ul), 1% normal mouse serum (50 ul) and 5% PEG (300 ul). The reaction solution was cultivated at 4° C. for further 4 hours and centrifuged, and the precipitate (pellets) was assayed for radioactivity by a gamma-counter, with a mean for three measurements being indicated.

Figure 8A:
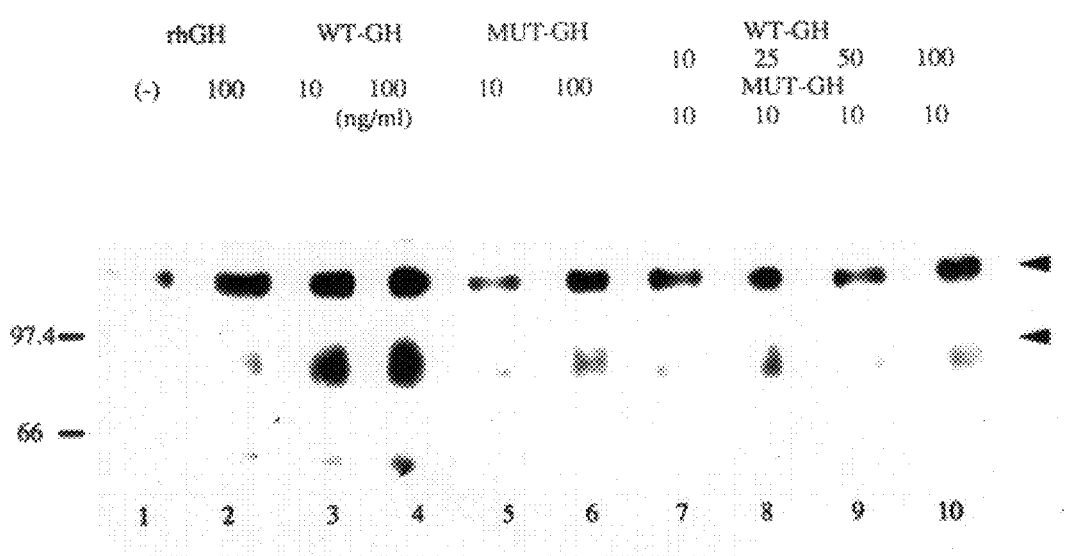

FIG. 8a is a photograph of an electrophoretic pattern showing a tyrosine phosphorylation in IM-9 cells being dependent on wild-type and mutant growth hormones.

IM-9 Cells were treated at 37° C. for 15 min in the presence and absence of 100 ng/ml of human growth hormone (Lanes 1 and 2); in the presence of wild-type growth hormone (Lane 3: 10 ng/ml, Lane; 100 ng/ml), mutant growth hormone (Lane 5; 10 ng/ml, Lane 6; 100 ng/ml) and mutant growth hormone of a constant concentration of 10 ng/ml, with increasing concentrations of wild-type growth hormone (Lane 7; 10 ng/ml, Lane 8; 25 ng/ml, Lane 9; 50 ng/ml, Lane 10; 100 ng/ml), respectively. Detergent lysates of these cells were immunoprecipitate with a phosphorylation-tyrosine specific antibody and analyzed by Western blotting with the same antibody conjugated to horseradish peroxidase. The molecular weights in unit of kilo-daltons were indicated on the left margin.

The symbols "arrow" designate the tyrosine-phosphorylated protein bands produced through action of growth hormone.

FIG. 8b is bar graphs showing the results of densitometry analysis for anti-phopshorylated tyrosine immunoblotting of p 120.

The amount of tyrosine-phosphorylated p-120 (IM-9 cells reported as JAK2) was determined by densitometry. Intensity of densitometry is expressed it relation to the one obtained as a control treated without growth hormone. Indicated is a mean (±SEM) for found values from three independent experiments, with statistical analysis being conducted by Student's t-test.

EXAMPLE 1

The following investigation was carried out on the blood samples drawn from the above-mentioned 5-years old boy with dwarfism showing a delayed bone age:

Hormone-assaying Method

A serum concentration of growth hormone was analyzed with use of an immunoradiometric assay kit manufactured by Pharmacia of Sweden, and biological activity of growth hormone was measured by the slightly modified Tanaka et al. (Tanaka T. et al., J. Cli. Endocrinol. Metab., 51: 1058, 1980) method, whereby in the Nb2 bioassay method, rabbit antiserum (NIDDK-anti-hORK-IC5; NIH) to human prolactin (hPRL) was added in a 100,000-fold dilution to inhibit through neutralization the growth-stimulating activity of human prolactin. By these procedures, the serum growth hormone was measured and analyzed with the patient with dwarfism and normal subjects as a control.

Isoelectric Focusing

Isoelectric focusing was performed by using the Tsventnitsky et al. (Tsventnitsky V. et al., Biochem. J., 307: 239, 1995) method; serum samples were electrofocused for separation with 1% HMPC (hydroxypropyl methylcellulose) –4% ampholine buffer at a pH gradient of pH 3.0 to 8.0 to thereby collect different fractions for the analysis of immunoactive growth hormone. Pooled serum samples from 10 normal subjects were used as a control.

Isolation and Genetic Analysis of the Gene for the Mutant Growth Hormone

Figure 4A:
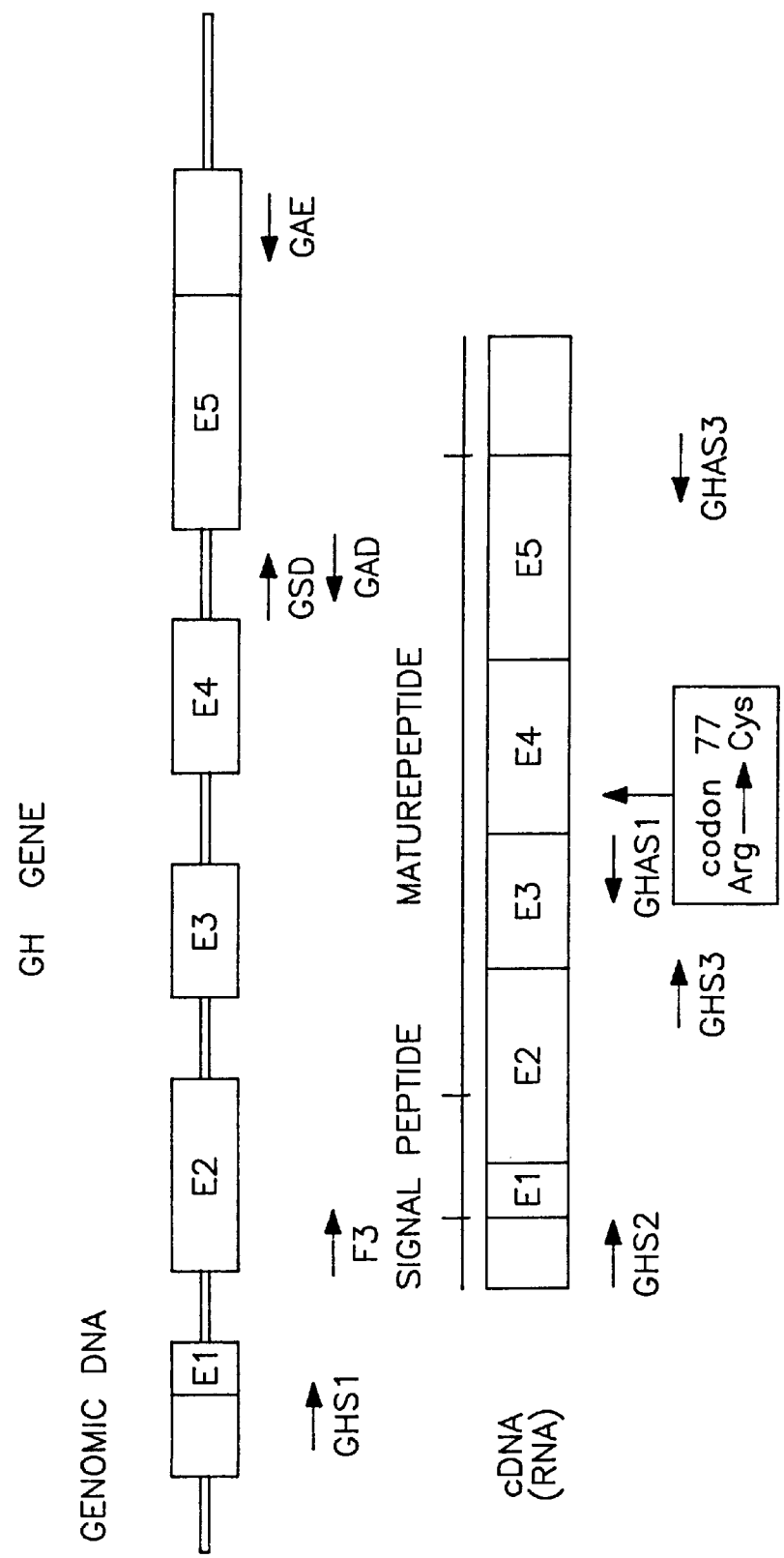
FIG. 4a is a genetic structure of the mutant growth hormone and a design of a primer for PCR amplification; Five exxon sites are indicated by the box, while the PCR primer by the arrow.
Figure 4B:
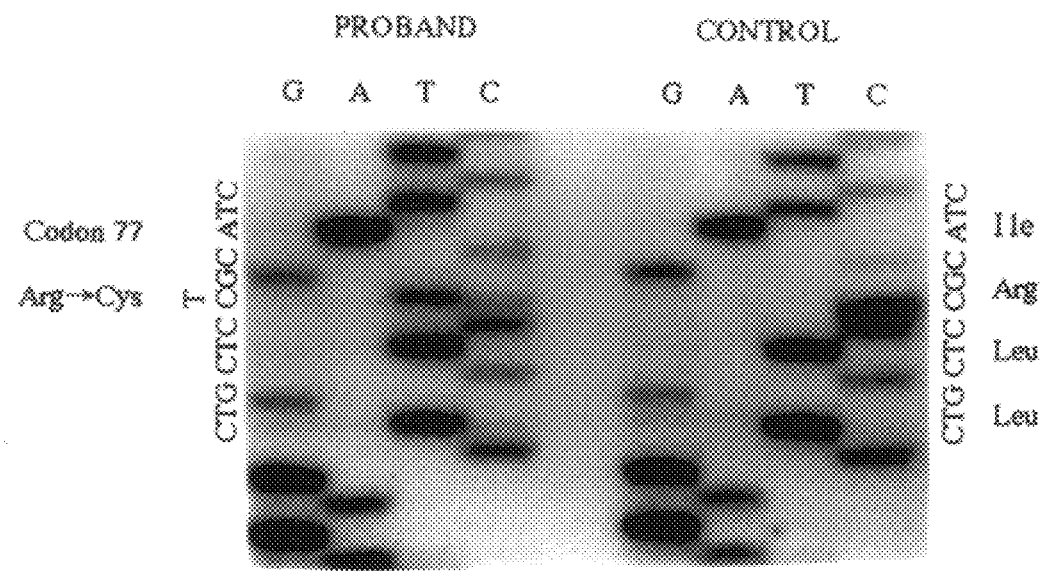
FIG. 4b is a photograph showing a DNA sequence (SEQ ID NO:21) of the mutant growth hormone, where alteration of arginine to cysteine at codon 77 is indicated (SEQ ID NO:22), as was determined by direct sequence analyses of genome DNA and RNA by use of PCR.

Genomic DNA was isolated from peripheral-blood leukocytes (Gross-Bellard M. et al., Eur. J. Biochem., 36: 32, 1973), and amplified by the PCR method (FIG. 4). The oliognucleotides, namely F3; 5'TATGAATTCCTCTGCCT-GCCCTGCC TCAAGAG3' (SEQ ID NO:4), GAD:5'CTAACACAGTCTCTCAAAGT3'(SEQ ID NO:5), GSD:5'ACTTTGAGA GACTGTGTTAG3' (SEQ ID NO:7), GAE:5'TGGAGTGGCAACTTCCAGGG3' (SEQ ID NO:8) and GHS1: 5'CTCAGGGTCCTGTGGACAGCTAC-CTAGCTGCA3' (SEQ ID NO:8), were used as a promoter for the amplification of the genomic DNA.

The PCR amplification was performed by the following procedure: with F3-GAD and GHS1-GAD, the first denaturation was effected at 92° C. for 3 min, followed by 35 cycles consisting of one minute of denaturation at 92° C., 2 minutes of annealing at 60° C. and 2 minutes of extension at 72° C., with the final cycle extension at 72° C. being performed for 7 min, and with GSD-GAE, the cycle consisting of one minute of denaturation at 92° C., 2 minutes of annealing at 60° C. and 2 minutes of extension at 72° C. was repeated 35 times, with only the final cycle extension being performed for 7 min.

The amplification products were extracted, then subcloned into pBS SK(+) (Stratagene, USA) or pT7blue (Novagem, USA) and sequenced with use of 373A DNA Sequencer (Perkin Elmer, USA). Furthermore, the site (Arg→Cys) of mutation in the DNA of the patient was identified, and the resultant PCR product was subjected to direct DNA sequencing with use of a double-strand DNA cycle sequencing kit (Gibco BRI, USA) in order to exclude a possibility of undergoing any misreactions in the PCR reaction. As a result, it was found that the patient's DNA had undergone substitution the arginine residue at the 77 position with a cysteine residue (FIG. 1).

RNA Analysis

Lymphocytes were separated by use of MPRM Ficoll-Hypaque (Flow Lab., USA), and total RNA was isolated by the conventional means (Maniates T. et al., Cold Spring Harbor Laboratory Press, 1982). cDNA was synthesized with 1 µg of RNA (Martynoff G. et al., Biochem. Biophys, Res. Commn., 93: 645, 1980), an the synthesized cDNA was used in the PCR reaction to amplify cDNA for the growth hormone gene. GHS2; 5'TGGACAGCTCACCTAGCT-GCA3' (SEQ ID NO:9), GHAS1; 5'GGATTTCTGTTGT-GTTTCCT3' (SEQ ID NO:10), GHS3; 5'TTGACACCTAC-CAGGAGTTT3' (SEQ ID NO:11) and GHAS3; 5'CTAGAAGCCACAGC TGCCCT3' (SEQ ID NO:12) were used as a oligonucleotide primer to perform the PCR amplification under the following conditions:

With GHS2-GHAS1, denaturation was effected at 92° C. for 3 min, and the cycle consisting of one minute of denaturation at 92° C., 1.5 minutes of annealing at 68° C. and 1.5 minutes of extension at 72° C. was repeated 40 times, with the final cycle extension being performed for 7 min.

With GHS3-GHAS3, the first denaturation was effected, followed by 40 cycles consisting of one minute of denaturation at 92° C., 1.5 minutes of annealing at 68° C. and 1.5 minutes of extension at 72° C. was repeated 40 times, with the final cycle extension being performed for 7 min., and the amplified products were subjected to base sequencing.

Construction of cDNAs for Wild-type and Mutant Growth Hormones cDNAs of two types of human growth hormone, wild-type and mutant-type, were amplified by PCR, while using a cDNA library prepared from human growth hormone producing pituitary adenoma cells (Clontech, USA). and the accuracy each of the identified structures for growth hormone cDNAs was confirmed by base sequencing for DNA.

Referring to the oligonucleotide primers used in the PCR procedures, GHS1 was utilized as a sense primer, while 5'TAAGAATTCGAGGGGTCACAGGGATGCCACCCC3' (SEQ ID NO:13) employed as an antisense primer.

PCR was performed under the reaction conditions: the first denaturation was effected at 92° C. for 3 min, and the cycle consisting of one minute of denaturation at 92° C., 1.5 minutes of annealing at 48° C. and 1.5 minutes of extension at 72° C. was repeated 40 times, with the final cycle extension being effected for 7 min.

cDNA of the mutant growth hormone was constructed with use of Transformer MT (Clontech, USA). To remove the signal sequence of cDNA of growth hormone, PCR amplification was conducted with a sense primer (5'GCGGATCCTTCC CAACCATTCCCTTATC3' (SEQ ID NO:14)) containing a BamH1 site incorporated artificially and GHAS1 as an antisense primer. The resultant cDNA was determined for base sequence by the direct base sequencing method to confirm the mutation (FIG. 1).

Expression and Functional Analysis of Wild-type (Normal) and Mutant Growth Hormones Each of the expression vectors for the production of wild-type and mutant growth hormones comprised a DNA sequence containing promoter operator PLOL derived from λ-bateriophage, a DNA sequence containing a N-utilization site capable of binding the anti-transcription terminating factor N-protein produced by host cells and a ribosome binding site capable of binding mRNAs of wild-type and mutant growth hormones to the ribosome inside host cells, ATG initiation codon and a restriction enzyme site for inserting the desired gene into the vector in phase with the ATG initiation codon ATG (Japanese Patent Publication No. 87780/1994).

The expression vectors were introduced into suitable host cells containing non heat-resistant repressor C1, for example, E. coli., and allowed to express wild-type and mutant growth hormones, respectively, when the host cells were heated at the repressor demolition temperature. Such expression products held at the amino terminal the methionine residue derived from the initiation codon, but elimination of such methionine residue with a specific aminopeptidase can yield the matured wild-type and mutant human growth hormones (Japanese Unexamined Patent Publication No. 500003/1982).

The transformed cells were cultivated, and the cell suspension was subjected to centrifugation or filtration to collect the cells, followed by lysis by means of physical and chemical techniques to isolate the mutant growth hormone.

The purification procedure was carried out by combinations of the known procedures, fractionation with ammonium sulfate, etc., gel filtration chromatography, ion exchange chromatography, affinity chromatography with use of antibody and normal-phase or reverse-phase high performance chromatography.

In order to prepare small-amount samples for experimental uses, cDNAs of wild-type and mutant growth hormones were cloned individually into a BamHI-EcoRI site of a plasmid (pGEXKG) and then incorporated into DH5α cells. The expression products were also prepared in the cell line fused with the glutathione-S-transferase gene supplied by Pharmacia of Sweden.

Figure 5:
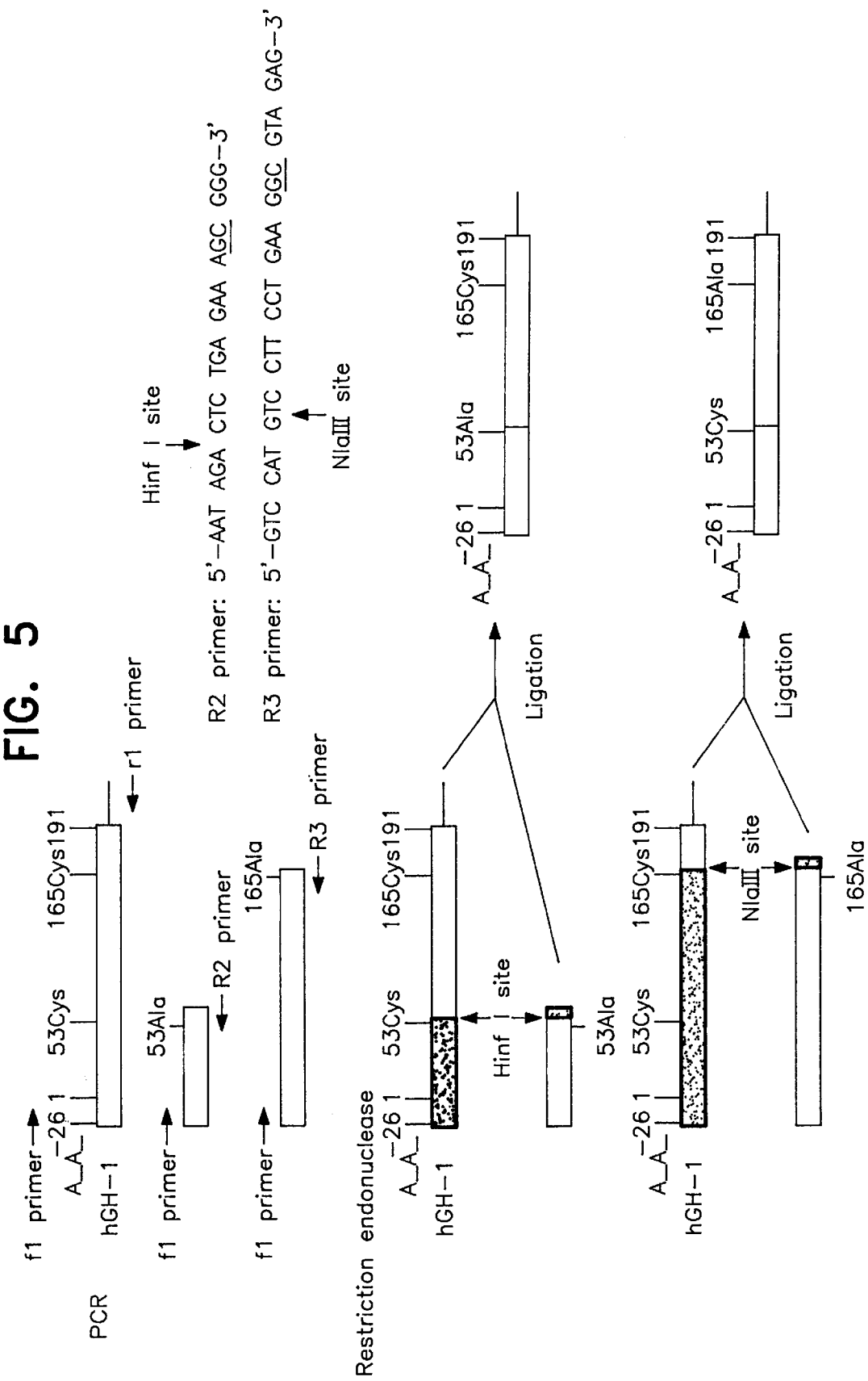
FIG. 5 is a flow sheet for the construction of cDNA for alteration of cysteine at 53 or 165 position to alanine, with the oligonucleotides showing the following sequences being used as a primer.

It was suggested that the intramolecular crosslinking between two cysteines within the recombinant mutant growth hormone obtained by the above procedures occurs in three different types, i.e. normal type (53–165) as well as two mutant types (53–77) and (77–165). Accordingly, cDNA prepared from lymphocytes of the patient was subjected to replacement for mutation by the procedure as shown in FIG. 5 to thereby produce cDNA in which cysteine at the 53 or 165 position was substituted with an alanine residue. In this case, there can be produced cDNA in which the cysteine at the 53 or 165 position is substituted with a serine residue.

These genes were expressed in *E. coli* to produce two kinds of mutant growth hormones in which a pair of cysteines formed crosslinking at the 77 and 165 positions (FIG. 2) and at the 53 and 77 positions (FIG. 3), respectively.

The bioactivity each of wild type and mutant growth hormones was determined by the IRMA and Nb2 bioassay system. The Nb2 bioassay was performed in the presence or absence of serum from the patient who showed neither growth hormone nor prolactin detected. Recombinant human growth hormone binding protein (rhGHBP) was added individually to the samples to the final concentrations of 0.1, 0.5 or 1 nM.

Competitive binding was studied in the human lymphoblastoma cell line IM-9 capable of expressing growth hormone receptor by the one-step receptor analysis method (Lesniak, M. A. et al., J. Biol. Chem., 249: 1661, 1974).

Direct binding of wild-type and mutant growth hormones to rhGHBP was investigated by use of immunoprecipitation.

Growth-hormone dependent tyrosine phosphorylation in IM-9 cells was detected by the Silva et al. method (Silva, M. D. et al., Endocrinology, 132: 101, 1993). Antiphosphorylation tyrosine monoclonal antibody (RC20: Transcution Laboratories, USA) was used in the immunoprecipitation and western blotting procedures, and antibody binding was visualized with an ECL kit manufactured by Amersham Co. of USA.

Isoelectric focusing demonstrated that in addition to the known wild type (normal) growth hormone, the mutant growth hormone was present in serum of the proband (patient) (FIG. 6).

In order to estimate whether or not the mutant growth hormone gene is bioreactive, the genes of the mutant and wild-type growth hormones were expressed in cells transformed with the expression vector possessing a promoter operator derived from λ-phages to thereby give the products, while the genes were also expressed in the GST fused protein system to obtain the products.

Both of the mutant and wild-type growth hormones were found to be immunoreactive by assay in IRMA cells. Their bioactivities were also measured by the Nb2 bioassay.

Despite the fact that both substances were found to exhibit a similar degree of bioactivity in the NB2 bioassay in a serum-free medium, the bioactivity of the mutant growth hormone decreased to less than half that of wild-type growth hormone in the patient's serum medium. In anticipation of the possibility of interference being caused by the growth hormone binding protein in the Nb2 bioassay system, the recombinant growth-hormone binding protein was added to the assay medium.

A ratio of bioactivity to immunoreactivity of the mutant growth hormone was found to decrease markedly to 0.45±0.05 ($p<0.05$) and 0.22±0.08 ($p<0.05$) in the presence of 0.5 nM and 1 nM of the recombinant growth-hormone binding protein, respectively. Such concentrations of the protein correspond to those of the actual physiologic binding protein in the peripheral blood.

Binding of [$^{125}$I]-labeled human growth hormone to human growth-hormone receptor in IM-9 cells was found to change in a concentration-dependent manner through replacement switching from wild-type to mutant growth hormones. The replacement with the mutant growth hormone exhibited a shoulder at the protein concentration in the range of $10^{-11}$ to $10^{-9}$ M.

Their individually found $IC_{50}$ values were almost equal, being at 0.84±0.30 nm and 0.86±0.41 nm, respectively.

However, the replacement with the mutant growth hormone did not proceed smoothly at the protein concentration in the range of $10^{-11}$ to $10^{-9}$ M (FIG. 7).

In addition, binding of [$^{125}$I]-labeled human growth hormone to the recombinant human growth-hormone binding protein in IM-9 cells was found to change in a concentration-dependent manner through replacement switching from wild-type to mutant growth hormones, as well.

The mutant growth hormone showed $IC_{50}$ of 0.12±0.02 nm (mean±SE, for 3 measurements) being remarkably lower than the counterpart of 0.68±0.08 nM for wild type growth hormone, and demonstrated about 6 times greater affinity for the binding protein than wild-type one.

Growth-hormone dependent tyrosine phosphorylation in the growth hormone receptor with use of IM-9 cells was compared between wild-type and mutant growth hormones by means of Western blotting.

In contrast with the fact that both recombinant growth hormone and wild type growth hormone, namely normal growth hormone, promoted tyrosine phosphorylation, the mutant growth hormone not only failed to exert any action on the tyrosine phosphorylation by itself but also inhibited markedly the phosphorylation induced by wild-type growth hormone. Inhibition of tyrosine phosphorylation was observed even when the mutant growth hormone was added simultaneously with wild-type growth hormone at a concentration of 1:10 (FIG. 8).

What is claimed:

1. A protein having an amino acid sequence selected from the group consisting of SEQ ID NO:15, SEQ ID NO:16 and SEQ ID NO:17.

2. DNA having a base sequence that encodes the protein according to claim 1.

3. An expression plasmid comprising the DNA according to claim 2.

4. A pharmaceutical composition useful for the treatment of gigantism or acromegaly which contains the protein according to claim 1 as an active ingredient, in combination with a pharmacologically acceptable carrier.

5. The protein of claim 1, wherein the amino acid sequence is SEQ ID NO: 15.

6. The protein of claim 1, wherein the amino acid sequence is SEQ ID NO: 16.

7. The protein of claim 1, wherein the amino acid sequence is SEQ ID NO: 17.

8. DNA having a nucleotide sequence selected from the group consisting of SEQ ID NO: 18, SEQ ID NO: 19 and SEQ ID NO: 20.

\* \* \* \* \*